United States Patent
Ofek et al.

(10) Patent No.: US 10,322,230 B2
(45) Date of Patent: Jun. 18, 2019

(54) SYSTEMS AND METHODS FOR CORRECTING AND PREVENTING OCCLUSION IN A CATHETER

(71) Applicant: C. R. Bard, Inc., Murray Hill, NJ (US)

(72) Inventors: Gidon Ofek, Salt Lake City, UT (US); Jay A. Muse, Salt Lake City, UT (US); Bret Hamatake, Grantsville, UT (US); Garrick T. Smith, Bountiful, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 15/619,219

(22) Filed: Jun. 9, 2017

(65) Prior Publication Data

US 2017/0354777 A1 Dec. 14, 2017

Related U.S. Application Data

(60) Provisional application No. 62/348,082, filed on Jun. 9, 2016.

(51) Int. Cl.
*A61M 5/14* (2006.01)
*A61M 5/145* (2006.01)
(Continued)

(52) U.S. Cl.
CPC ........ *A61M 5/1452* (2013.01); *A61M 1/0062* (2013.01); *A61M 1/0066* (2013.01);
(Continued)

(58) Field of Classification Search
CPC .............. A61M 1/0062; A61M 1/0066; A61M 1/3659; A61M 2005/1403;
(Continued)

(56) References Cited

U.S. PATENT DOCUMENTS 3,941,122 A 3/1976 Jones
4,155,362 A 5/1979 Jess
(Continued)

FOREIGN PATENT DOCUMENTS

WO 2014043650 A2 3/2014
WO 14149648 A1 9/2014
(Continued)

OTHER PUBLICATIONS

Atar S, Neuman Y, Miyamoto T, Chen M, Birnbaum Y, Luo H, Kobal S, Siegel Rj. "Synergism of aspirin and heparin with a low-frequency non-invasive ultrasound system for augmentation of in-vitro clot lysis." J Thromb Thrombolysis. Jun. 2003; 15(3):165-9.
(Continued)

*Primary Examiner* — Imani N Hayman
(74) *Attorney, Agent, or Firm* — Rutan & Tucker, LLP

(57) ABSTRACT

A patency device for catheter assemblies and other elongate tubular devices used for establishing access to an interior body portion of a patient is disclosed. The patency device establishes and preserves patency of one or more lumens defined by the catheter assembly by providing impulses of positive pressure to fluid disposed in the lumen of the catheter assembly. In one embodiment, the patency device comprises a fluid reservoir configured to provide a fluid path to at least one lumen of the catheter assembly, and a pressure input portion. The pressure input portion is configured to provide pressure for one or more impulses of positive pressure to a fluid disposed within the lumen. The impulses are configured to dislodge occlusions that may have formed in the lumen. A negative pressure can then be provided to the lumen to aspirate the occlusion.

35 Claims, 7 Drawing Sheets

(51) Int. Cl.
  *A61M 1/00* (2006.01)
  *A61M 39/22* (2006.01)
  *A61M 25/00* (2006.01)
  *A61M 1/36* (2006.01)
  *A61M 5/158* (2006.01)
  *A61M 5/168* (2006.01)

(52) U.S. Cl.
  CPC .......... *A61M 1/3659* (2014.02); *A61M 25/00* (2013.01); *A61M 39/225* (2013.01); *A61M 2005/1403* (2013.01); *A61M 2005/1588* (2013.01); *A61M 2005/16863* (2013.01); *A61M 2025/0019* (2013.01); *A61M 2205/3344* (2013.01)

(58) Field of Classification Search
  CPC .. A61M 2025/0019; A61M 2205/3344; A61M 25/00; A61M 39/225; A61M 5/1452
  See application file for complete search history.

(56) References Cited

U.S. PATENT DOCUMENTS

| | | |
|---|---|---|
| 4,191,184 A | 3/1980 | Carlisle |
| 4,446,867 A | 5/1984 | Leveen et al. |
| 4,551,041 A | 11/1985 | Coon et al. |
| 4,692,139 A | 9/1987 | Stiles |
| 4,698,058 A | 10/1987 | Greenfeld et al. |
| 4,781,677 A | 11/1988 | Wilcox |
| 4,808,153 A | 2/1989 | Parisi |
| 4,870,953 A | 10/1989 | DonMicheal et al. |
| 4,959,050 A | 9/1990 | Bobo, Jr. |
| 5,006,304 A | 4/1991 | Franklin et al. |
| 5,267,565 A | 12/1993 | Beard |
| 5,269,291 A | 12/1993 | Carter |
| 5,273,027 A | 12/1993 | Sekino et al. |
| 5,318,014 A | 6/1994 | Carter |
| 5,427,118 A | 6/1995 | Nita et al. |
| 5,431,663 A | 7/1995 | Carter |
| 5,480,379 A | 1/1996 | La Rosa |
| 5,536,242 A | 7/1996 | Willard et al. |
| 5,592,866 A | 1/1997 | Sher |
| 5,916,192 A | 6/1999 | Nita et al. |
| 5,925,016 A | 7/1999 | Chornenky et al. |
| 5,935,146 A | 8/1999 | McEwen et al. |
| 6,001,069 A | 12/1999 | Tachibana et al. |
| 6,007,514 A | 12/1999 | Nita |
| 6,024,718 A | 2/2000 | Chen et al. |
| 6,027,450 A | 2/2000 | Brown et al. |
| 6,126,619 A | 10/2000 | Peterson et al. |
| 6,135,977 A | 10/2000 | Drasler et al. |
| 6,142,987 A | 11/2000 | Tsugita |
| 6,149,596 A | 11/2000 | Bancroft |
| 6,210,404 B1 | 4/2001 | Shadduck |
| 6,371,928 B1 | 4/2002 | McFann et al. |
| 6,398,714 B1 | 6/2002 | Verkerke et al. |
| 6,433,464 B2 | 8/2002 | Jones |
| 6,435,189 B1 | 8/2002 | Lewis et al. |
| 6,602,264 B1 | 8/2003 | McGuckin, Jr. |
| 6,617,760 B1 | 9/2003 | Peterson et al. |
| 6,652,547 B2 | 11/2003 | Rabiner et al. |
| 6,676,637 B1 | 1/2004 | Bonnette et al. |
| 6,685,657 B2 | 2/2004 | Jones |
| 6,689,109 B2 | 2/2004 | Lynn |
| 6,723,064 B2 | 4/2004 | Babaev |
| 6,740,059 B2 | 5/2004 | Flaherty |
| 6,852,097 B1 | 2/2005 | Fulton, III |
| 6,855,123 B2 | 2/2005 | Nita |
| 6,921,371 B2 | 7/2005 | Wilson |
| 6,945,951 B1 | 9/2005 | Bonnette et al. |
| 6,979,293 B2 | 12/2005 | Hansmann et al. |
| 7,144,381 B2 | 12/2006 | Gertner |
| 7,220,233 B2 | 5/2007 | Nita et al. |
| 7,220,239 B2 | 5/2007 | Wilson et al. |
| 7,297,131 B2 | 11/2007 | Nita |
| 7,335,180 B2 | 2/2008 | Nita et al. |
| 7,341,569 B2 | 3/2008 | Soltani et al. |
| 7,393,338 B2 | 7/2008 | Nita |
| 7,648,478 B2 | 1/2010 | Soltani et al. |
| 7,686,825 B2 | 3/2010 | Hauser et al. |
| 7,717,853 B2 | 5/2010 | Nita |
| 7,789,830 B2 | 9/2010 | Ishida et al. |
| 7,828,762 B2 | 11/2010 | Wilson et al. |
| 7,918,822 B2 | 4/2011 | Kumar et al. |
| 7,955,293 B2 | 6/2011 | Nita et al. |
| 7,993,308 B2 | 8/2011 | Rule et al. |
| 8,043,251 B2 | 10/2011 | Nita et al. |
| 8,052,704 B2 | 11/2011 | Olson |
| 8,062,316 B2 | 11/2011 | Patel et al. |
| 8,083,707 B2 | 12/2011 | Tosaya et al. |
| 8,152,753 B2 | 4/2012 | Nita et al. |
| 8,162,924 B2 | 4/2012 | Boyden et al. |
| 8,167,831 B2 | 5/2012 | Wilson et al. |
| 8,317,770 B2 | 11/2012 | Miesel et al. |
| 8,348,880 B2 | 1/2013 | Messerly et al. |
| 8,366,620 B2 | 2/2013 | Nita |
| 8,414,569 B2 | 4/2013 | Manwaring et al. |
| 8,617,096 B2 | 12/2013 | Nita et al. |
| 8,622,911 B2 | 1/2014 | Hossack et al. |
| 8,632,560 B2 | 1/2014 | Pal et al. |
| 8,647,293 B2 | 2/2014 | Nita |
| 8,758,519 B2 | 6/2014 | Waldmann et al. |
| 8,827,953 B2 | 9/2014 | Rocha-Singh |
| 8,852,166 B1 | 10/2014 | Keilman et al. |
| 8,956,386 B2 | 2/2015 | Hauser et al. |
| 8,999,070 B2 | 4/2015 | MacKenzie |
| 9,028,748 B2 | 5/2015 | Zumeris et al. |
| 9,107,590 B2 | 8/2015 | Hansmann et al. |
| 9,144,693 B2 | 9/2015 | Appelman et al. |
| 9,198,680 B2 | 12/2015 | Fraser et al. |
| 9,254,144 B2 | 2/2016 | Nguyen et al. |
| 2002/0151825 A1 | 10/2002 | Rubenchik et al. |
| 2004/0019318 A1 | 1/2004 | Wilson et al. |
| 2004/0210140 A1 | 10/2004 | Rabiner et al. |
| 2005/0027265 A1 | 2/2005 | Maki et al. |
| 2005/0209578 A1 | 9/2005 | Christian Evans et al. |
| 2005/0215942 A1 | 9/2005 | Abrahamson et al. |
| 2005/0220711 A1 | 10/2005 | Katz |
| 2006/0173387 A1 | 8/2006 | Hansmann et al. |
| 2006/0241524 A1 | 10/2006 | Lee et al. |
| 2006/0264809 A1 | 11/2006 | Hansmann et al. |
| 2007/0167798 A1 | 7/2007 | Cai et al. |
| 2007/0213681 A1 | 9/2007 | Manna et al. |
| 2007/0239027 A1 | 10/2007 | Nita |
| 2007/0265560 A1 | 11/2007 | Soltani et al. |
| 2008/0097206 A1 | 4/2008 | Chomas et al. |
| 2008/0125657 A1 | 5/2008 | Chomas et al. |
| 2008/0243153 A1 | 10/2008 | Nguyen et al. |
| 2009/0018472 A1 | 1/2009 | Soltani et al. |
| 2009/0118663 A1 | 5/2009 | Rockley et al. |
| 2009/0157003 A1 | 6/2009 | Jones et al. |
| 2010/0010393 A1 | 1/2010 | Duffy et al. |
| 2010/0094201 A1 | 4/2010 | Mallaby |
| 2010/0217276 A1 | 8/2010 | Garrison et al. |
| 2010/0262215 A1 | 10/2010 | Gertner |
| 2010/0286708 A1 | 11/2010 | Rittman |
| 2011/0046522 A1 | 2/2011 | Chan et al. |
| 2011/0087147 A1 | 4/2011 | Garrison et al. |
| 2011/0112564 A1 | 5/2011 | Wolf |
| 2012/0059285 A1 | 3/2012 | Soltani et al. |
| 2012/0179073 A1 | 7/2012 | Nita |
| 2012/0232434 A1 | 9/2012 | Nita et al. |
| 2012/0232435 A1 | 9/2012 | Nita et al. |
| 2012/0232465 A1 | 9/2012 | Nita et al. |
| 2012/0238916 A1 | 9/2012 | Nita et al. |
| 2012/0238946 A1 | 9/2012 | Nita et al. |
| 2012/0289889 A1 | 11/2012 | Genstler et al. |
| 2013/0116603 A1 | 5/2013 | Nita |
| 2013/0331738 A1 | 12/2013 | Borrelli |
| 2014/0107481 A1 | 4/2014 | Wulfman |
| 2014/0155922 A1 | 6/2014 | Nita |
| 2015/0025543 A1 | 1/2015 | Nita et al. |
| 2015/0025544 A1 | 1/2015 | Nita et al. |
| 2015/0094595 A1 | 4/2015 | Havel et al. |

(56) References Cited

U.S. PATENT DOCUMENTS

| | | |
|---|---|---|
| 2015/0141817 A1 | 5/2015 | Chen et al. |
| 2015/0190660 A1 | 7/2015 | Serge et al. |
| 2015/0196309 A1 | 7/2015 | Matsubara et al. |
| 2015/0320432 A1 | 11/2015 | Adams |
| 2015/0352379 A1 | 12/2015 | Appelman et al. |

FOREIGN PATENT DOCUMENTS

| | | |
|---|---|---|
| WO | 14151209 A1 | 9/2014 |
| WO | 15029039 A1 | 3/2015 |
| WO | 2015074032 A1 | 5/2015 |
| WO | 15157330 A1 | 10/2015 |

OTHER PUBLICATIONS

Doomernik De, Schrijver Am, Zeebregts Cj, de Vries Jp, Reijnen Mm. "Advancements in catheter-directed ultrasound-accelerated thrombolysis." J Endovasc Ther. Jun. 2011; 18(3):418-34.

Ekos EkoSonic Ultrasound Endovascular System—designed to treat intravascular clots using ultrasound technology https://www.btg-im.com/en-US/Ekos/Products/EkoSonic-EndoVascular-System, last accessed Jun. 9, 2017.

Emmi-dent—Ultrasound emitting oral toothbrush designed to prevent biofilm formation and remove bacteria on teeth (http://www.emmi-dent.com) Last accessed Jun. 9, 2017.

Joyce E, Phull Ss, Lorimer Jp, Mason T J. "The development and evaluation of ultrasound for the treatment of bacterial suspensions. A study of frequency, power and sonication time on cultured *Bacillus* species." Ultrason Sonochem. 2003.

Mason T J, Joyce E, Phull Ss, Lorimer Jp. "Potential uses of ultrasound in the biological decontamination of water." Ultrason Sonochem. Oct. 2003;10(6):319-23.

Mourad Pd, Roberts Fa, Mcinnes C. "Synergistic use of ultrasound and sonic motion for removal of dental plaque bacteria." Compend Contin Educ Dent. Jul. 2007;28(7):354-8.

Neuman Y, Rukshin V, Tsang V, Atar S, Miyamoto T, Luo H, Kobal S, Thompson T, Birnbaum Y, Horzewski M, Siegel Rj, Kaul S. "Augmentation of in-stent clot dissolution by low frequency ultrasound combined with aspirin and heparin. An exvivo canine shunt study" Thromb Res. 2003;112(1-2):99-104.

Owens Ca. "Ultrasound-Enhanced Thrombolysis: EKOS EndoWave Infusion Catheter System." Seminars in Interventional Radiology. 2008;25(1):37-41.

Pajek D, Burgess A, Huang Y, Hynynen K. "High-intensity focused ultrasound sonothrombolysis: the use of berfluorocarbon droplets to achieve clot lysis at reduced acoustic power." Ultrasound Med Biol. Sep. 2014;40(9):2151-61.

Wright C, Hynynen K, Goertz D. "In vitro and in vivo high-intensity focused ultrasound thrombolysis." Invest Radial. Apr. 2012;47(4):217-25.

SYSTEMS AND METHODS FOR CORRECTING AND PREVENTING OCCLUSION IN A CATHETER

CROSS-REFERENCE TO RELATED APPLICATIONS

This application claims the benefit of U.S. Provisional Patent Application No. 62/348,082, filed Jun. 9, 2016, and titled "Systems and Methods for Correcting and Preventing Occlusion in a Catheter," which is incorporated herein by reference in its entirety.

BRIEF SUMMARY

Briefly summarized, embodiments of the present invention are directed to a patency device for catheter assemblies and other elongate tubular devices used for establishing access to an interior body portion of a patient. The patency device establishes and/or preserves patency of one or more lumens defined by the catheter assembly by providing impulses of positive pressure to fluid disposed in the lumen of the catheter assembly.

In one embodiment, the patency device comprises a fluid reservoir configured to provide a fluid (or establish a fluid path) to at least one lumen of the catheter assembly, and a pressure input portion. The pressure input portion is configured to provide pressure for one or more impulses of positive pressure to a fluid disposed within the lumen. The impulses are configured to dislodge occlusions that may have formed in the lumen. A negative pressure can then be provided to the lumen to aspirate the occlusion and remove it from the catheter assembly.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to catheter assemblies and other elongate tubular devices used for establishing access to an interior body portion of a patient. A peripherally inserted central catheter ("PICC") is one example of such a catheter assembly. In particular, solutions and methods for establishing and preserving the patency of one or more lumens defined by the catheter assembly are disclosed. Examples of patency devices that may be employed are disclosed according to particular embodiments, discussed below.

Figure 1:
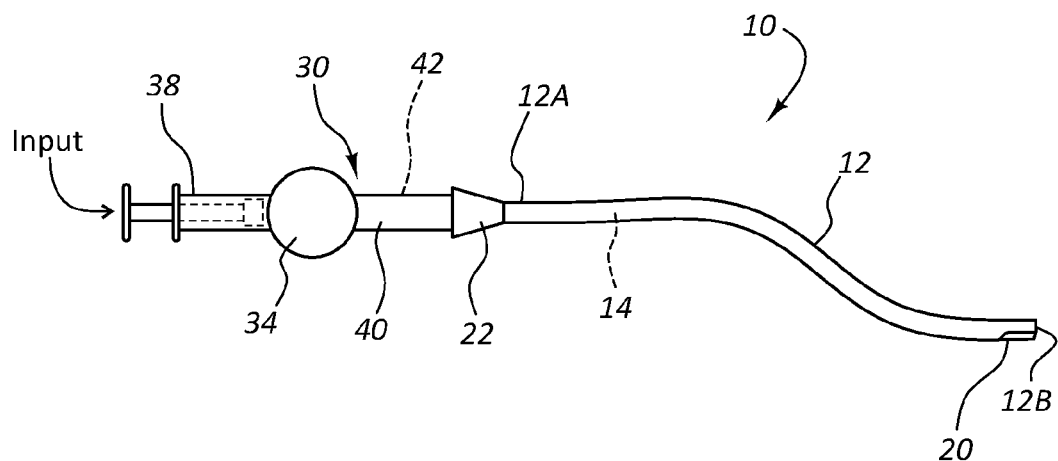
FIG. 1 is a simplified view of a catheter assembly and a patency device attached thereto according to one embodiment.

Reference is first made to FIG. 1, which generally depicts various details of a catheter assembly ("catheter"), generally designated at 10, and a patency device, to be described further below, in accordance with one embodiment. As shown, the catheter 10 includes an elongate catheter tube 12 that defines a lumen 14 extending between a proximal end 12A and a distal end 12B of the catheter tube. A luer connector 22 or other suitable connector is included at the proximal end 12A of the catheter tube 12. In other embodiments, the catheter can include a bifurcation hub at the proximal end of the catheter tube, with one or more extension legs proximally extending therefrom.

Though shown here as defining a single lumen 14, the catheter 10 in other embodiments can define two or more lumens. Also, though shown as a PICC, the catheter in other embodiments can include other catheter types, such as dialysis, CVC, PIV, urinary, arterial, balloon catheters, etc. Thus, the discussion herein is not intended to be limiting.

FIG. 1 further shows details regarding a patency device 30 configured to operably connect on a temporary basis with the catheter 10 and provide patency to the catheter tube lumen 14, according to one embodiment. Generally, the patency device 30 includes a fluid reservoir 34 that is configured, together with a pressure input portion 38, to provide one or more relatively short-duration impulses, also referred to herein as positive pressure impulses, of high-pressure fluid to the lumen 14 of the catheter tube 12. Such impulses, when performed periodically, are configured to prevent the formation of thrombus or other occlusion in the lumen 14, especially at the distal end thereof. These short-duration, high pressure impulses can also be used to clear the lumen after occlusions have formed therein.

In greater detail, the pressure input portion 38 of the patency device 30 includes a mechanical input, such as a manual or motor-controlled plunger-type syringe, to impart pressure impulses to fluid contained in the fluid reservoir 34. The fluid reservoir 34 is configured to hold an amount of fluid that can be directed into the lumen(s) 14 of the catheter tube 12 prior to or in conjunction with the pressure impulses produced by the pressure input portion 38. In one embodiment and as seen below, the fluid reservoir 34 serves as a hydraulic accumulator to store pressurized fluid, produced by the pressure input portion 38, before its release to the lumen(s) 14.

It is noted that other types of pressure input portions can be utilized to provide high-pressure fluid impulses, including electrical and acoustic actuators, voice coil actuators, linear actuators, piezoelectric motors, vibrational drums and membrane, etc., for instance.

A catheter connector interface 40 defining a lumen 42 is included to enable the patency device 30 to operably connect to the luer connector 22 (or other portion) of the catheter 10 and provide a conduit through which the high pressure fluid can pass from the fluid reservoir 34 to the lumen(s) 14 of the catheter tube 12. Note that in one embodiment the connector interface 40 is a sterile item to bridge between the non-sterile patency device 30 and the catheter 10. In this way, the connector interface 40 can be manufactured as a disposable, sterile item, while the patency device 30 is reusable.

In operation, the patency device 30 emits periodic, relatively short-duration, relatively high-pressure bursts, or impulses, in the distal direction through the fluid-filled lumen 14 of the catheter tube 12. These impulses are produced by the pressure input portion 38 in conjunction with the pressure portion 34 and transmitted through the lumen 42 of the patency device 30 to the catheter tube lumen 14 via the connector interface 40 luer connector 22. It is appreciated that the pressure of the impulses, the impulse duration, the rest period between impulses, the frequency of successive impulses, etc., can be adjusted and varied according to the particular patency procedure being performed for the catheter 10.

Figure 2:
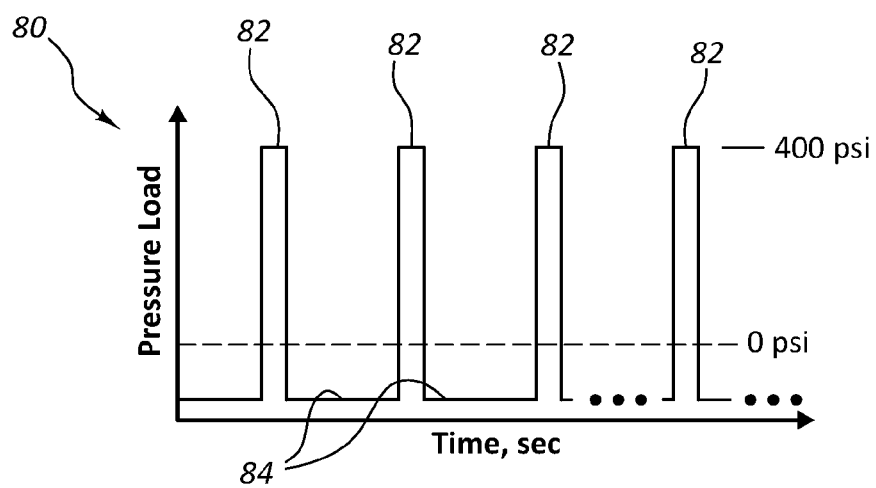
FIG. 2 is a graph showing a pressure profile for the patency device of FIG. 1.

FIG. 2 depicts a graph of a pressure profile 80 (including fluid pressure vs. time) produced by the patency device 30 during operation. The pressure profile 80 includes time on the x-axis and impulse pressure on the y-axis for operation of the patency device 30. As shown, the patency device 30 provides short-duration, relatively high-pressure impulses through the fluid present in the catheter tube lumen 14 interspersed by relatively longer rest periods 84 of negative baseline pressure provided to the catheter tube lumen. The negative baseline pressure present between impulses enables any occlusion dislodged by the impulses to be sucked proximally up the catheter tube lumen 14 and removed therefrom, thus preventing the dislodged occlusion from entering the bloodstream from the distal end 12B of the catheter tube 12. Note that the rest periods in other embodiments can include a reduction to a neutral pressure or lower (but still positive) pressure or to varying pressures over time as may be desired.

FIG. 2 further shows that successive impulse peaks 82 that represent the short-duration high-pressure fluid impulses are shown on the graph of the pressure profile 80. In the present embodiment, the pressure peaks 82 are each characterized by a rise-time phase of about 30 milliseconds, a holding high-pressure phase of about 200 milliseconds, and a pressure reduction phase of about 40 milliseconds. It is appreciated that these phases of the pressure peaks 82 can vary from the values given herein, and each pressure peak can vary in phase characteristics from previous and/or subsequent peaks. Also, the magnitude and duration of the impulses can vary from what is described herein and from one another.

In one embodiment, the pressure peaks 82 are modified by a controller of the patency device 30 so as to be customizable by the user. The rest periods 84 between the high-pressure fluid impulses (represented by the pressure peaks 82) can also be varied in duration, baseline pressure, etc.

In the present embodiment, the maximum pressure achieved by the impulses is about 400 psi, though this can vary according to desired application, catheter lumen design, type or size of occlusion, catheter tube length, etc. In one embodiment, it is appreciated that the maximum pressure of the impulses may exceed the burst pressure strength rating of the catheter tube 12 in one embodiment, but as the impulses are of relatively short duration, no rupturing or failure of the catheter 10 occurs.

As mentioned above, the high-pressure fluid impulses travel from the patency device 30 and into the catheter 10 so as to travel down the fluid-filled lumen 14 of the catheter tube 12. In one embodiment, the fluid filling the fluid path of the patency device and the catheter tube lumen 14 is a 0.9% saline solution, though other fluids may also be acceptably used. Note that the use of other fluids can necessitate altering the impulse characteristics (e.g., impulse pressure, impulse duration, rest period duration, etc.). As noted above, the high-pressure fluid impulses impinge on an occlusion (such as a clot or fibrin sheath) or other obstruction that has formed in the lumen 14, typically at or proximate the distal end 12B of the catheter tube 12. The occlusion is dislodged by the high-pressure impulses, which are strong enough to dislodge the occlusion but are not of sufficient duration to push it out the distal end 12B of the catheter tube 12. The subsequent negative pressure rest period following each impulse can act to prevent escape of the clot from the catheter tube 12, in one embodiment. In addition, a suction process can be performed by the patency device 30 to withdraw the clot proximally from the catheter tube 12 and catheter 10 and into the patency device, where it may be disposed of. In this way, any clot or occlusion present in the catheter 10 can be acceptably removed.

Figure 3:
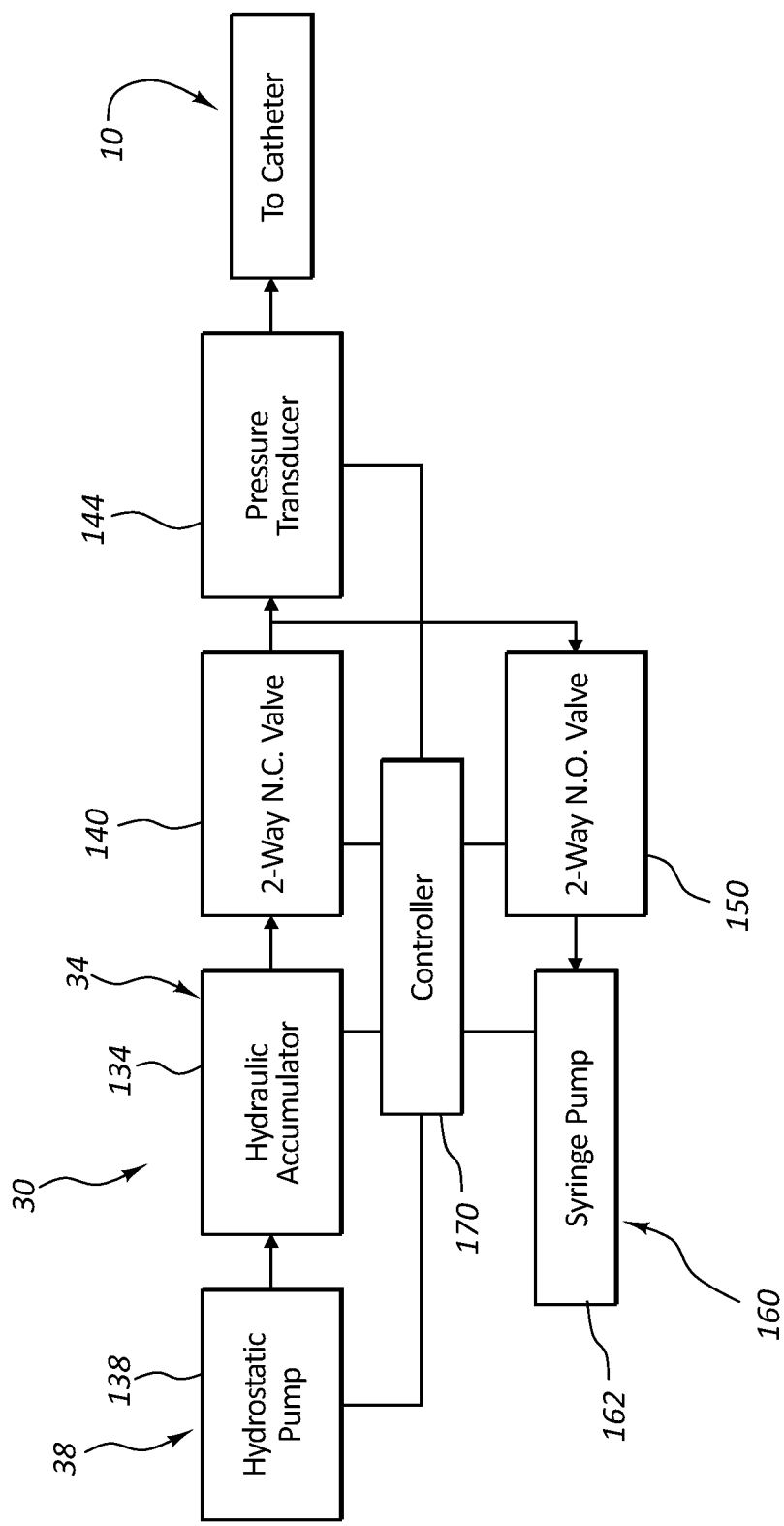
FIG. 3 is a block diagram of a patency device according to one embodiment.

FIG. 3 depicts the patency device 30 according to one embodiment. As shown, the patency device 30 includes a hydrostatic pump 138 that serves as the pressure input portion 38 for providing hydraulic pressure to fluid contained and maintained at pressure in a hydraulic accumulator ("accumulator") 134 that serves as the fluid reservoir 34. A two-way, normally closed ("N.C.") valve 140 is disposed at and operably connected at its fluid inlet to a fluid outlet of the accumulator 134 via a fluid line. A pressure transducer 144 is operably interposed between the fluid outlet of the N.C. valve 140 and the luer connector 22 or other suitable inlet to the catheter. As mentioned above, in this and other embodiments the connector interface 40 (FIG. 1) can be used to operably connect the patency device 30 to the catheter 10. Note that the fluid lines between the various components discussed herein can include tubing or other suitable modes for fluid transport.

A two-way, normally open ("N.O.") valve 150 is interposed between the N.C. valve 140 and the transducer 144 via a fluid line connected to the N.O. valve fluid inlet. A vacuum input portion 160 for providing negative pressure in the patency device 30 is operably connected to the fluid outlet of the N.C. valve 150. In the present embodiment, a syringe pump 162 serves as the vacuum input portion 160, though other suitable components can also be employed, such as a vacuum pump. A controller 170 is operably connected to the aforementioned components of the patency device 30 to govern their operation. The controller 170 in one embodiment includes a power source, a printed circuit board including a processor, etc.

Figure 4A:
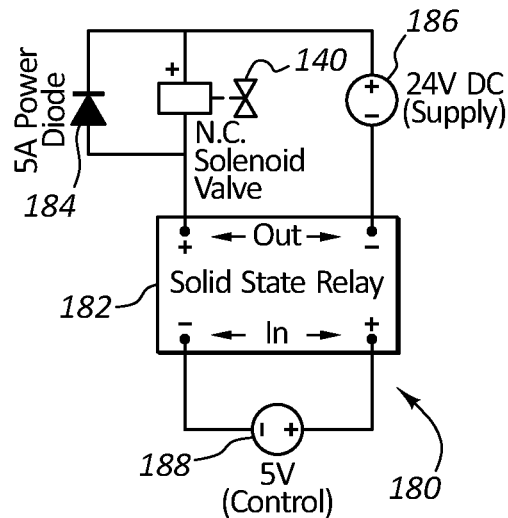
FIGS. 4A and 4B are schematic diagrams of valve assemblies for the patency device of FIG. 3.
Figure 4B:
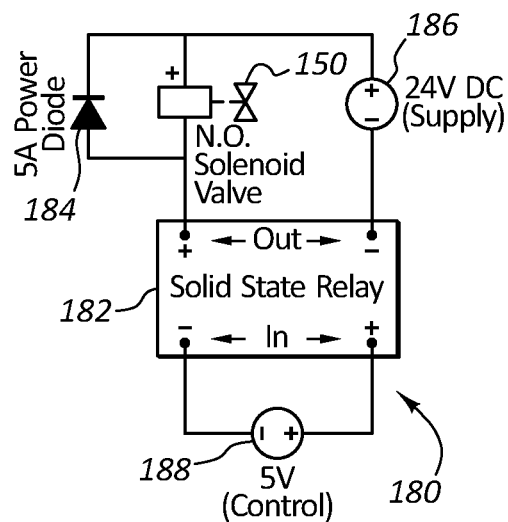

FIG. 4A depicts various details regarding a valve control assembly 180 associated with the N.C. valve 140 shown in the patency device 30 of FIG. 3, according to one embodiment. As shown, the valve control assembly 180 includes a relay 182 and a power diode operably interconnected with the N.C. valve 140. A power supply 186 is included for the N.C. valve 140, as is a power supply 188 for the relay 182. FIG. 4B shows a similar configuration for the valve control assembly 180 associated with the N.O. valve 150 of the patency device 30 of FIG. 3, including a relay 182 and a power diode operably interconnected with the N.O. valve. A power supply 186 is included for the N.O. valve 150, as is a power supply 188 for the relay 182. The valve control assemblies 180 for the N.C. valve 140 and the N.O. valve 150 assist in governing operation of the N.C. and N.O. valves during operation of the patency device 30. In the present embodiment, the N.C. valve 140 and the N.O. valve 150 are gate-valve types of valves, though it is appreciated that other suitable types of valves can be utilized. In another embodiment, the functionality of the N.C. valve 140 and the N.O. valve 150 can be combined into a single valve, such as a three-way valve, with the fluid lines being arranged so as to provide such an embodiment. In such a single valve embodiment, the single three-way valve is operated to alternately provide the impulses of positive pressures as well as the negative baseline pressures/negative impulses.

The patency device 30 of FIG. 3 is operably attached to luer connector 22 of the catheter 10 when a patency procedure (a procedure to clear the catheter tube lumen(s) 14 of an occlusion or to prevent formation thereof) is desired by a clinician or catheter user. In operation, the patency device 30 first provides fluid pressure via actuation—either manually or by automatic/motor modes—of the hydrostatic pump 138. The pressurized fluid is received from the pump 138 by the accumulator 134, which stores the fluid in a pressurized state until needed. The N.O. valve 150 is maintained in an open state at the beginning and during the procedure to maintain a negative base pressure in the system except at those times when the N.C. valve 140 is opened to provide the fluid impulses. The controller 170 or other suitable component can control valve opening/closing.

The controller 170 determines the number, frequency, rest periods, etc., of the impulses to be delivered by the patency device 30 to the catheter tube lumen(s) 14. The N.C. valve 140 is opened and close repeatedly at predetermined time intervals to provide a series of fluid impulses from the accumulator, through the N.C. valve and into the lumen 14 of the catheter 10. During each impulse when the N.O valve 140 is opened, the N.O valve 150 is shut so as to prevent impulse fluid from entering the N.O. valve and diverting to the syringe pump 162 instead of entering the catheter tube lumen 14 as desired. The impulses are propagated distally down the lumen 14, which is fluid-filled prior to commencement of the patency operation so as to provide a propagation medium for the impulses.

Between each impulse and after the series of impulses has ended, the N.C. valve 140 closes and the N.O. valve 150 opens to provide a negative baseline pressure (provided by the syringe pump 162 or other suitable device) in the catheter tube lumen 14 and enable any occlusion dislodged by the impulses to be suctioned proximally out of the lumen, through the N.O. valve to the syringe pump 162. An appropriate capture reservoir or the like can be operably connected to the syringe pump to provide for retention of occlusions and fluid if needed. The controller 170 is utilized to precisely control the opening/closing of the N.C. valve 140 and the N.O. valve 150 so as to provide the impulses and the negative baseline pressure to the lumen 14 as desired.

In one embodiment, it is appreciated that the baseline negative pressure periods existing between the positive pressure impulses can be replaced or supplemented with relatively short-duration impulses of negative pressure to further assist in occlusion dislodgement. Subsequent negative baseline pressure can then be used to remove the occlusion to the lumen 14. In one embodiment, the response time of the valves 140 and 150 is sufficiently fast to enable the positive pressure impulses to be followed in quick succession by the negative baseline pressure or negative pressure impulse.

The pressure transducer 144 is utilized and controlled by the processor 170 to measure the pressure of the impulses delivered to the catheter tube lumen 14 by the patency device 30. As mentioned, the pressure level of the impulses can be varied or determined according to a variety of factors, including catheter length, catheter lumen size, burst strength, impulse duration, rest period duration, other catheter configuration, etc. In one embodiment, the pressure of each impulse can be chosen from a range of from about 30 psi to about 120 psi, though other pressure below and above this are possible. Also, frequency of the impulses, or impulse frequency, can be set according to a predetermined pattern and can vary according to a number of factors such as those described immediately above and can range in one embodiment from about 1 to over about 150 Hz, though other frequency ranges are also possible. In one embodiment, the impulse frequency is set to match the resonant frequency of the catheter 10 itself, thus enabling improved propagation of the impulses distally through the lumen 14. In one example, for instance, the resonant frequency of a 3 Fr single lumen catheter assembly was found to be about 30 Hz for catheter tube lengths of from about 35 cm to about 55 cm. The resonant frequency will vary according to a number of catheter characteristics. In one embodiment, for instance, resonant frequencies for various catheters vary from about 15 Hz to about 50 Hz, though other frequencies are possible.

In one embodiment, the impulse frequency is above about 20 KHz, thus performing as an ultrasound impulse signal to dislodge lumen occlusions or maintain lumen patency. These ultrasonic signals are of sufficient frequency, intensity, and duty cycle as to dislodge the occlusion(s) present in the lumen(s) 14. In one embodiment, the patency device 30 can include a an ultrasound module operably connectable to the luer connector 22 or extension leg of the catheter 10 and further includes an ultrasound transducer for providing ultrasonic impulses to the fluid-filled lumen 14. The patency device 30 can further include ports to enable fluids or other substances to be infused into or aspired from the catheter tube lumen(s) 14, such as antimicrobial agents, etc.

Note that the patency device 30 is either externally powered or can include its own power source, such as a battery. Note further that in one embodiment that the controller 170 can enable customization of the characteristics of the impulses, rest periods, baseline pressure, etc. by the user.

It is appreciated that periodic use of the patency devices described herein can also serve to prevent the formation of an occlusion by preventing initial adherence and growth of the occlusion in the first place, as mentioned herein. In one embodiment, the patency device is self-operating, thus serving as a passive solution to preventing occlusions.

Note that in one embodiment a pressure regulator can be employed to provide and/or maintain pressurized fluid in the patency device 30. Note also that it is appreciated that adjustments may be made to the pressure of the impulses to compensate for pressure loss/attenuation as a function of the distance the impulse travels distally through the catheter tube lumen 14.

In light of the above, it is appreciated that in one embodiment, a method for providing patency to at the lumen(s) 14 the catheter assembly 10 comprises disposing a fluid in the lumen of the catheter tube 12 of the catheter; and propagating a plurality of impulses of positive pressure through the fluid disposed in the lumen, noting that the impulses are propagated in a predetermined pattern.

Figure 5:
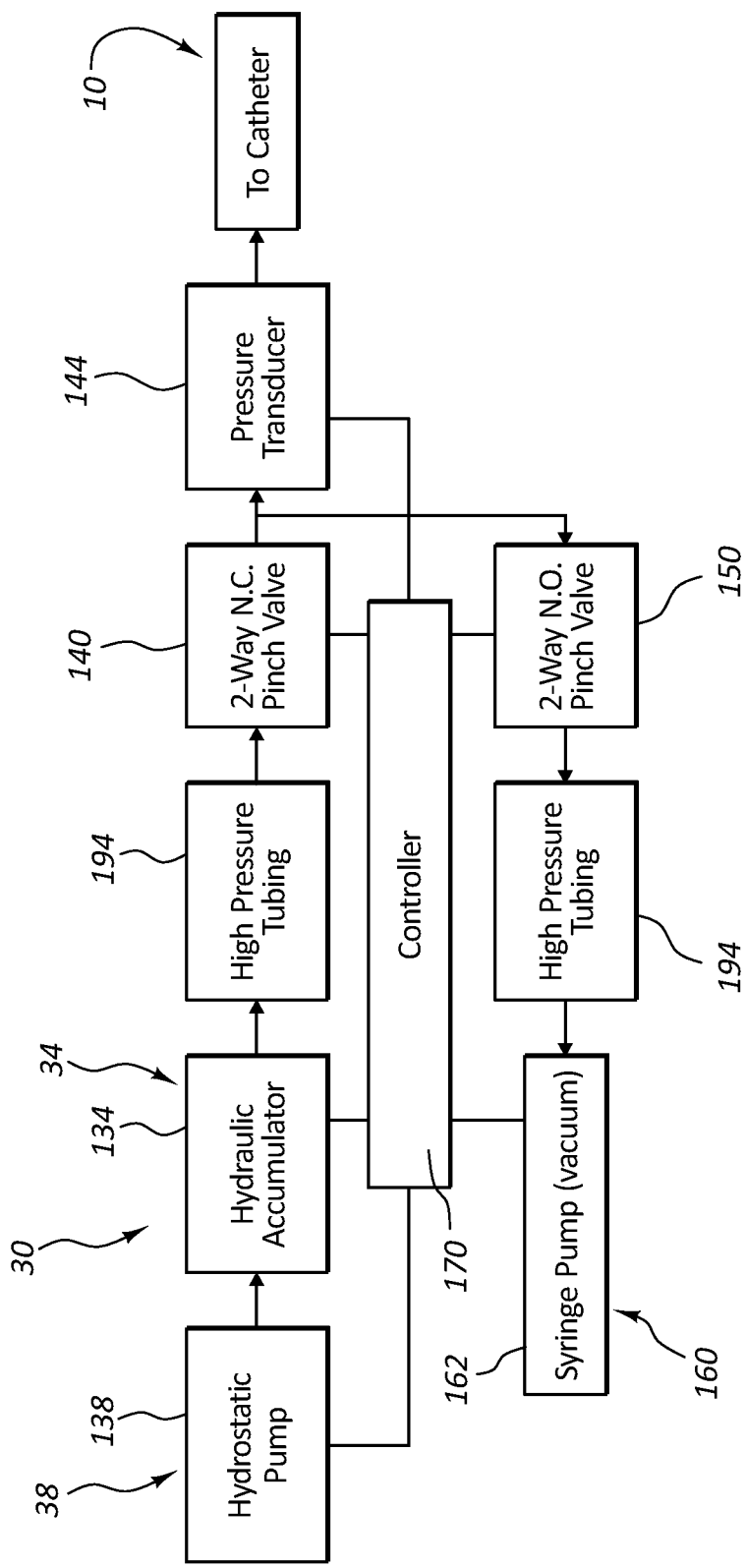
FIG. 5 is a block diagram of a patency device according to one embodiment.

The patency device of FIG. 5 replaces the gate valve-type of valves with tubing pinch valves for the N.O valve 140 and the N.O. valve 150. Such valves operate by pinching off a portion of the tubing that comprises the fluid lines, such as the illustrated high pressure tubing 194 proximate the N.O. pinch valve 150, so as to stop fluid flow therethrough. The valve releases the pinch-off of the tubing to enable fluid flow anew therethrough. These and other valve types are therefore contemplated.

Figure 6:
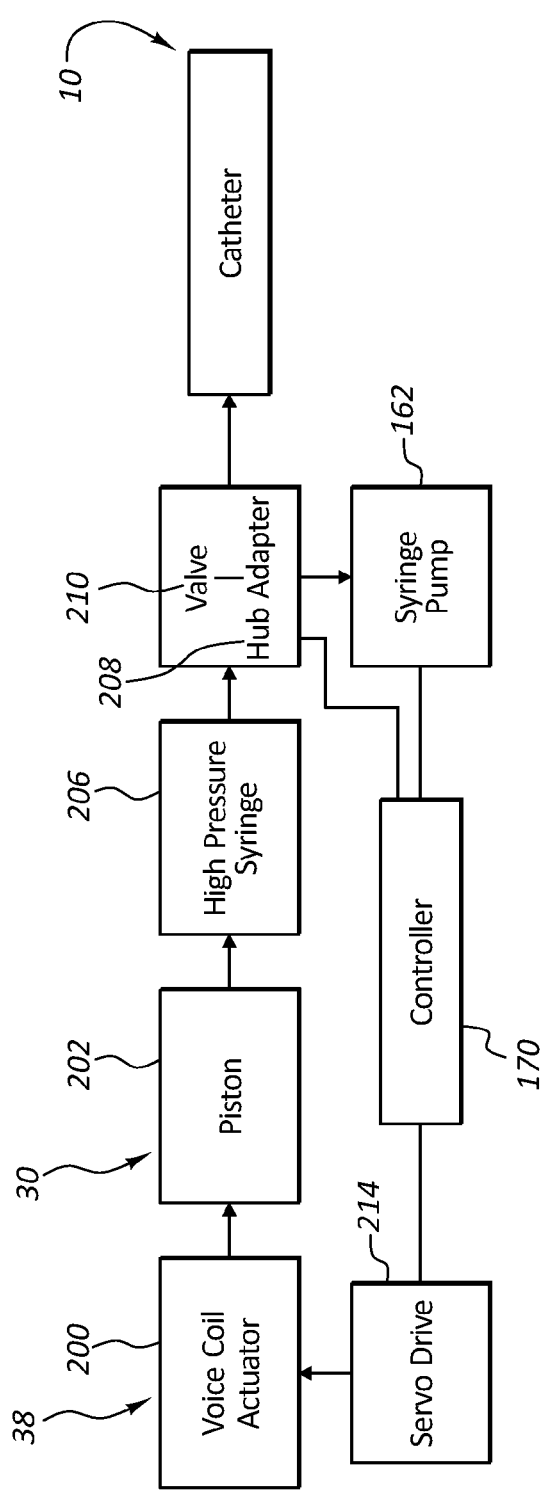
FIG. 6 is a block diagram of a patency device according to one embodiment.

FIG. 6 depicts details of the patency device 30 according to another embodiment, wherein the pressure input portion 38 includes an actuator, such as a voice coil actuator 200 configured to provide mechanical movement for the formation of the desired fluid pressure impulses. A servo drive 214 is operably connected to the voice coil actuator 200 to assist in actuator function. A piston 202 (or plunger or the like) is operably connected to the voice coil actuator 200, which in turn is operably connected to the fluid reservoir 34, here a fluid-containing syringe 206. The syringe 206 in the present embodiment is a high pressure syringe. The piston 202 is sized to be received within a proximal end of the syringe 206 so as to enable the piston to transfer the mechanical movements of the voice coil actuator to the fluid present in the syringe to create the desired impulses. Impulses produced in the fluid of the syringe 206 are forwarded past a valve 210 and into the lumen 14 of the catheter tube 12. A hub adapter 208 is included in the present embodiment to enable the valve 210 to operably connect to the catheter 10.

The valve 210 is operable, such as by 170 controller, to selectively open to enable the impulses produced by the aforementioned components to pass through to the catheter lumen 14. At all other times during a patency procedure, the valve 210 is switched to enable a negative baseline pressure to be imparted to the catheter lumen 14 via the syringe pump 162 in manner similar to embodiments discussed above. In one embodiment, pressure of the impulses produced by the patency device 30 of FIG. 6 are measured from about 60 psi to more than about 100 psi, though this can vary according to system design.

Figure 7:
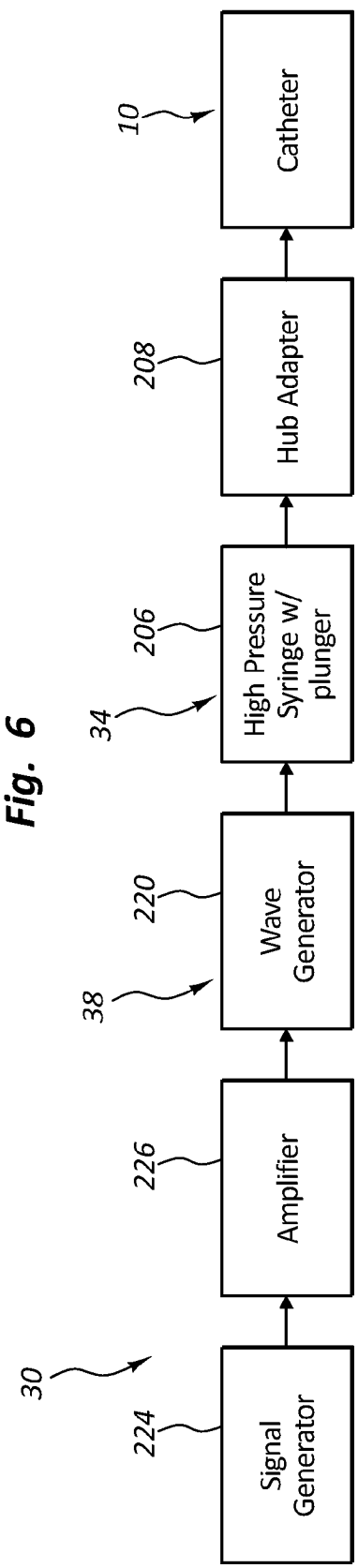
FIG. 7 is a block diagram of a patency device according to one embodiment.

FIG. 7 depicts details of the patency device 30 according to another embodiment, wherein the pressure input portion 38 includes a wave generator 220, such as a loudspeaker, to produce energy for the formation of the desired fluid impulses. A signal generator 224 produces voltage waveforms, or driving signals, to actuate the wave generator in a desired pattern for the impulses, the signals of the signal generator being amplified by an amplifier 226. In one embodiment, pressure of the impulses produced by the patency device 30 of FIG. 7 are measured at about 40 psi or less, though this can vary according to system design.

A piston, such as a plunger, is operably connected to the movable cone of the loudspeaker of the wave generator 220 is received within the fluid-containing syringe 206, serving as the fluid reservoir 34. Operation of the loudspeaker moves the cone thereof in accordance with the driving signals received and amplified by the signal generator 224 and amplifier 226, which in turn moves the plunger in accordance with the driving signals. The fluid contained in syringe 106 is moved by the plunger, which produces the desired fluid impulses that are propagated distally through the lumen 14 of the catheter 10 via the hub adapter 208. In one embodiment, the impulses produced by the patency device of FIG. 7 are in a frequency range of from about 1 to about 200 Hz, though a variety of other frequencies are possible.

The embodiments of the patency device 30 shown and described in connection with FIGS. 3, 5, 6, and 7 are therefore representative of a multitude of a variety of patency devices that can be employed to provide fluid impulses for the dislodgement of occlusive material within the lumen of a catheter and/or to maintain the patency of the lumen, free from occlusions.

Figure 8:
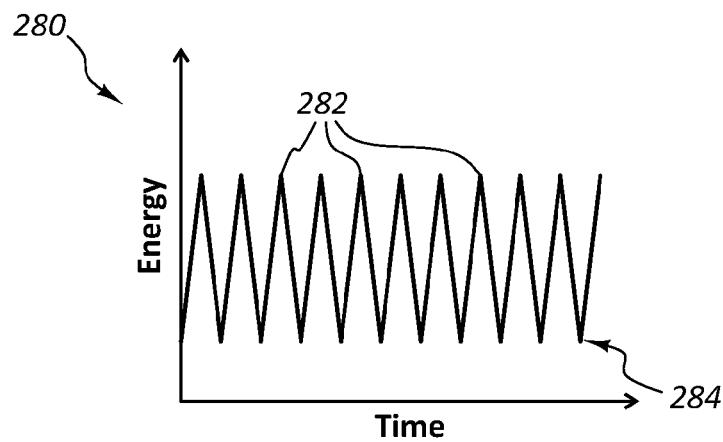
FIG. 8 is a pressure profile for a patency device according to one embodiment.
Figure 9:
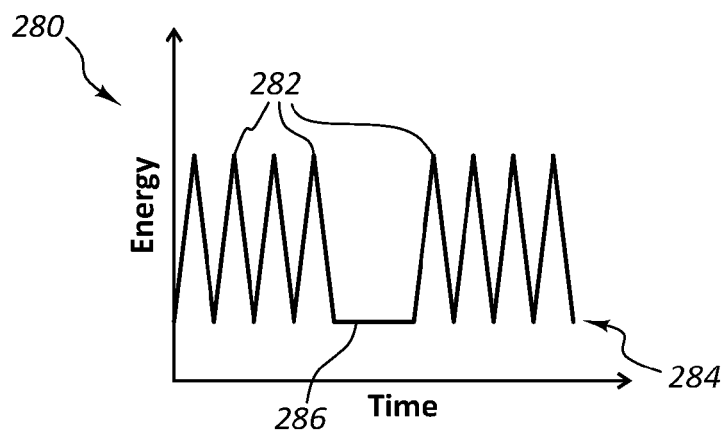
FIG. 9 is a pressure profile for a patency device according to one embodiment.
Figure 10:
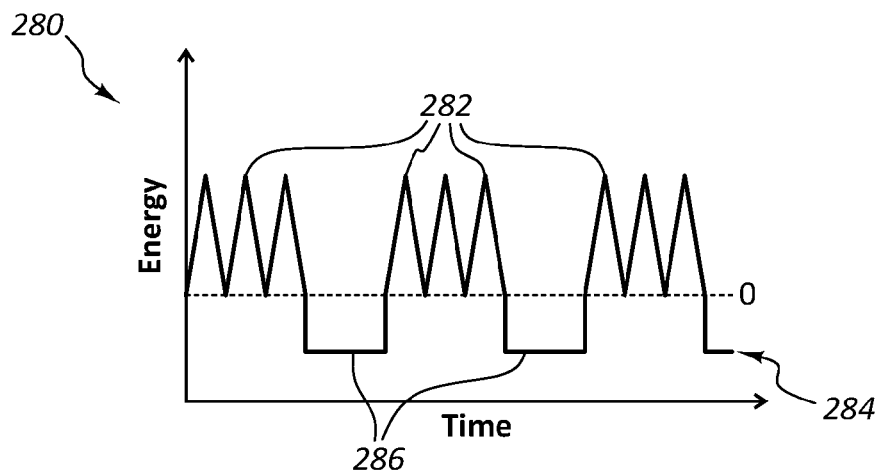
FIG. 10 is a pressure profile for a patency device according to one embodiment.

FIGS. 8-10 depict various operation cycles for the positive pressure impulses produced by the present patency device, such as the patency device 30 shown in FIG. 6, for instance. FIG. 8 shows a pulse profile 280 including a continuous series of equal (in terms of energy, pressure) impulses delivered to the catheter tube lumen 14 (FIG. 1) at a set impulse frequency and returning to a baseline pressure 284 before starting the next impulse. The frequency can be any one or more of a variety of impulse frequencies, including ultrasonic frequencies (e.g., above 20 KHz).

In FIG. 9, a series of groups of impulses is shown, wherein groups of impulses are separated by rest periods 286 of nominal baseline pressure 284, such as a low positive pressure, which pattern is useful for when no occlusion is present but impulses are used to keep the lumen 14 patent.

In FIG. 10, a series of groups of impulses is shown, wherein groups of impulses are separated by rest periods 286 of negative baseline pressure 284 to enable aspiration from the catheter 10 of any occlusions dislodged by the impulses, as discussed further above. In these and the other examples herein, note that the number of impulses in each group can vary according to user desire and/or a pre-set predetermined pattern, as can the pressure, frequency, etc. Note that frequency use of the patency device 30 can vary from continuously, hourly, daily, weekly, occasionally, etc., depending on whether the intended use is prophylactic or corrective, the amount of occlusion present, etc.

Figure 11:
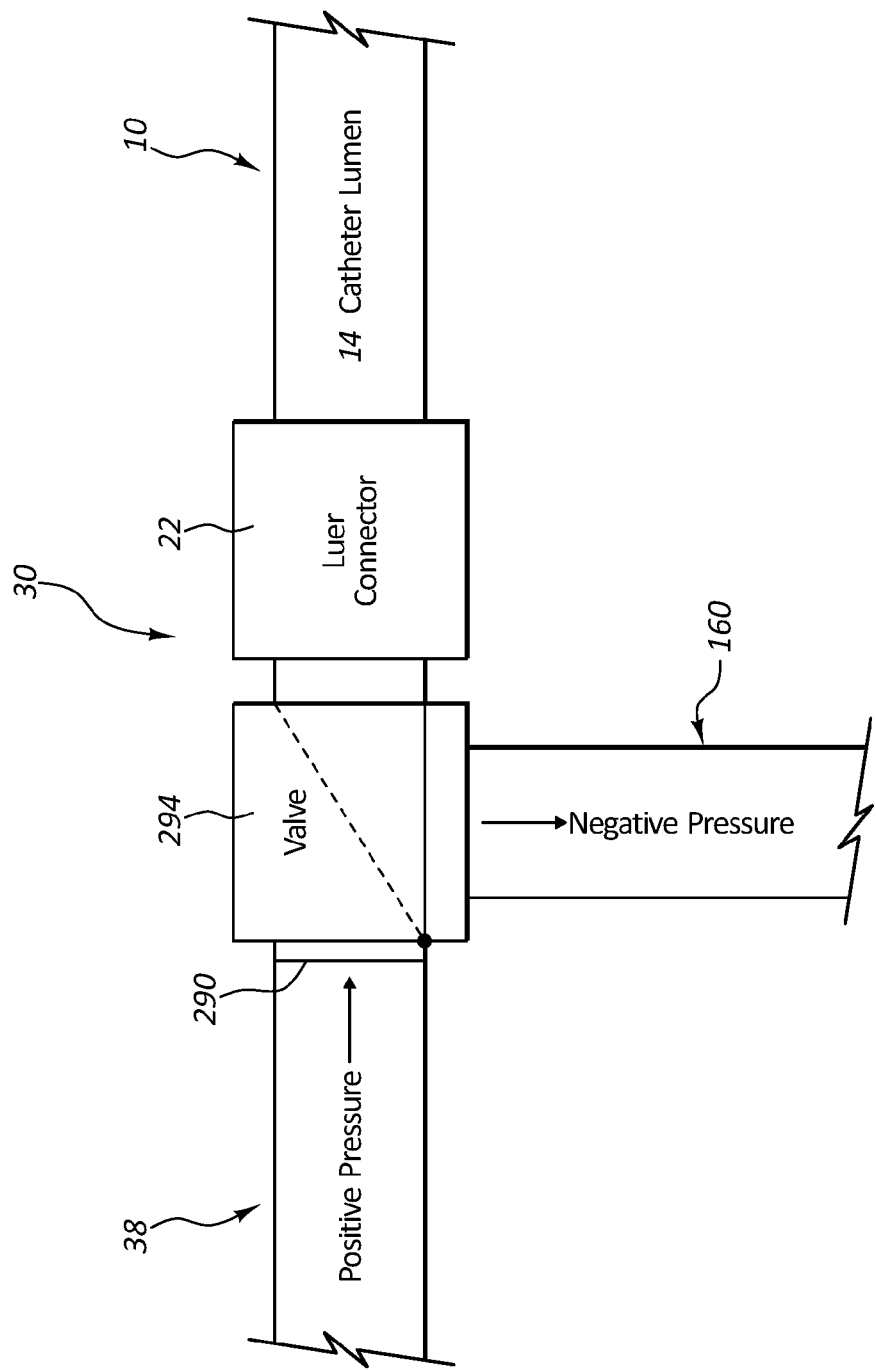
FIG. 11 is a block diagram of a patency device according to one embodiment.

FIG. 11 depicts details of the patency device 30 including the pressure input portion 38, including a hydrostatic pump or other suitable component as described herein or appreciated. A membrane 290 is included and configured to move/vibrate when acted upon by the positive pressure produced by the pressure input portion 38, thus producing impulses of positive pressure that are propagated through fluid disposed in a valve 294, such as a three-way valve, before travelling through the fluid-filled luer connector 22 and the lumen 14 of the catheter 10 to provide patency thereto. A vacuum input portion 160 is provided to supply negative baseline pressure/negative pressure impulses to fluid in the lumen 14 when the valve 294 is actuated to provide fluid communication therebetween. It is appreciated that no fluid reservoir 34 is included in the present embodiment. The embodiment shown in FIG. 11 can include a T-connector to provide the illustrated structure, in one embodiment.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A patency device for providing patency to at least one lumen of a catheter assembly, the patency device comprising:
 a fluid reservoir configured to provide a fluid path to the at least one lumen of the catheter assembly;
 a pressure input portion having a distal end connected to the fluid reservoir, the pressure input portion configured to provide pressure for at least one impulse of positive pressure to a fluid disposed within the at least one lumen; and
 an interface portion having a proximal end connected to the fluid reservoir, and a distal end connected to the at least one lumen.

2. The device as defined in claim 1, wherein the at least one impulse is configured to dislodge an occlusion disposed in the at least one lumen.

3. The device as defined in claim 1, wherein the patency device is further configured to provide a temporary negative pressure to the fluid disposed in the at least one lumen.

4. The device as defined in claim 3, wherein the temporary negative pressure is provided by a vacuum input portion of the patency device.

5. The device as defined in claim 4, wherein the vacuum input portion includes at least one of a syringe pump and a vacuum pump.

6. The device as defined in claim 4, wherein a normally open valve is included with the vacuum input portion.

7. The device as defined in claim 6, wherein a normally closed valve is included with the pressure input portion.

8. The device as defined in claim 7, wherein the normally open valve is configured to provide the temporary negative pressure to the fluid disposed in the at least one lumen, the normally open valve configured to close upon opening of the normally closed valve, the normally closed valve configured to provide the at least one impulse to the fluid disposed in the at least one lumen.

9. The device as defined in claim 1, wherein the at least one impulse includes a series of impulses at a predetermined impulse frequency and wherein the interface portion is disposable and provides a sterile barrier between the catheter assembly and the patency device.

10. The device as defined in claim 9, wherein the predetermined impulse frequency is at least 20 KHz.

11. The device as defined in claim 1, wherein the pressure input portion provides multiple series of the impulses in a predetermined impulse pattern, each series including at least one impulse.

12. The device as defined in claim 11, wherein each of the series of the impulses is separated by a rest period.

13. The device as defined in claim 12, wherein the patency device is configured to provide a negative pressure to the fluid disposed within the at least one lumen during each rest period.

14. The device as defined in claim 1, wherein the patency device is configured to provide the at least one impulse at a pressure of at least 30 psi.

15. The device as defined in claim 1, wherein the patency device is configured to provide the at least one impulse at a pressure that exceeds a burst pressure strength rating of a catheter tube of the catheter assembly.

16. The device as defined in claim 1, further comprising a pressure transducer configured to provide data relating to a pressure within a fluid line of the patency device.

17. The device as defined in claim 1, further comprising a controller configured to govern operation of the patency device, the controller including a processor.

18. The device as defined in claim 1, wherein the pressure input portion includes at least one of a hydrostatic pump, an actuator, and a wave generator.

19. The device as defined in claim 1, wherein the fluid reservoir includes at least one of a hydraulic accumulator and a syringe.

20. The device as defined in claim 1, wherein the at least one impulse includes a rise-time phase of about 30 milliseconds, a holding high-pressure phase of about 200 milliseconds, and a pressure reduction phase of about 40 milliseconds.

21. A patency device for providing patency to at least one lumen of a catheter assembly, the patency device comprising:
 a fluid path to the at least one lumen of the catheter assembly;
 a pressure input portion configured to provide pressure for at least one impulse of positive pressure to a fluid disposed within the at least one lumen; and
 a vacuum input portion configured to provide a temporary negative pressure to the fluid disposed in the at least one lumen.

22. The device as defined in claim 21, wherein the vacuum input portion includes at least one of a syringe pump and a vacuum pump.

23. The device as defined in claim 21, wherein a normally open valve is included with the vacuum input portion.

24. The device as defined in claim 23, wherein a normally closed valve is included with the pressure input portion.

25. The device as defined in claim 24, wherein the normally open valve is configured to provide the temporary negative pressure to the fluid disposed in the at least one lumen, the normally open valve configured to close upon opening of the normally closed valve, the normally closed valve configured to provide the at least one impulse to the fluid disposed in the at least one lumen.

26. The device as defined in claim 21, wherein the pressure input portion includes one of a hydrostatic pump and an actuator, and wherein the fluid path includes a hydraulic accumulator operably connected to the hydrostatic pump.

27. The device as defined in claim 21, wherein the at least one impulse includes a series of impulses at a predetermined impulse frequency.

28. A method for providing patency to at least one lumen of a catheter assembly, the method comprising:
 disposing a fluid in the at least one lumen of a catheter tube of the catheter assembly; and
 propagating a plurality of impulses of positive pressure through the fluid disposed in the at least one lumen, the plurality of impulses propagated in a predetermined pattern.

29. The method as defined in claim 28, wherein propagating the plurality of impulses comprises propagating at least one series of impulses at a predetermined impulse frequency.

30. The method as defined in claim 29, further comprising propagating a first series of impulses followed by a rest period, and propagating a subsequent series of impulses.

31. The method as defined in claim 28, wherein propagating the plurality of impulses further comprises propagating the plurality of impulses at a pulse frequency of at least about 20 KHz.

32. The method as defined in claim 28, further comprising providing a negative pressure to the fluid disposed in the at least one lumen to aspirate occlusions dislodged by the plurality of impulses.

33. The method as defined in claim 28, further comprising providing a negative pressure to the fluid disposed in the at least one lumen between impulses of positive pressure to aspirate occlusions dislodged by the plurality of impulses.

34. The method as defined in claim 28, wherein propagating the plurality of impulses includes propagating the plurality of impulses in a distal direction with respect to the at least one lumen of the catheter tube.

35. The method as defined in claim 28, wherein propagating the plurality of impulses comprises propagating at least one series of impulses at a predetermined impulse frequency, the predetermined impulse frequency substantially matching a resonant frequency of the catheter assembly.

* * * * *